United States Patent
Choi et al.

(10) Patent No.: US 10,604,591 B2
(45) Date of Patent: Mar. 31, 2020

(54) MODIFIED AND CONJUGATED DIENE-BASED POLYMER AND METHOD FOR PREPARING THEREOF

(71) Applicant: LG Chem, Ltd., Seoul (KR)

(72) Inventors: Seung Ho Choi, Daejeon (KR); Ji Eun Kim, Daejeon (KR); Won Mun Choi, Daejeon (KR); Cheol Jae Kim, Daejeon (KR)

(73) Assignee: LG Chem, Ltd. (KR)

( * ) Notice: Subject to any disclaimer, the term of this patent is extended or adjusted under 35 U.S.C. 154(b) by 124 days.

(21) Appl. No.: 15/580,101

(22) PCT Filed: Dec. 22, 2016

(86) PCT No.: PCT/KR2016/015078
§ 371 (c)(1),
(2) Date: Dec. 6, 2017

(87) PCT Pub. No.: WO2017/111487
PCT Pub. Date: Jun. 29, 2017

(65) Prior Publication Data
US 2018/0162959 A1 Jun. 14, 2018

(30) Foreign Application Priority Data
Dec. 22, 2015 (KR) .................. 10-2015-0184240

(51) Int. Cl.
| | | |
|---|---|---|
| C08C 19/25 | (2006.01) | |
| C07F 7/18 | (2006.01) | |
| B60C 1/00 | (2006.01) | |
| C08K 5/00 | (2006.01) | |
| C08K 5/16 | (2006.01) | |
| C08K 5/54 | (2006.01) | |
| C08F 36/04 | (2006.01) | |
| C08C 19/22 | (2006.01) | |
| C08F 8/30 | (2006.01) | |
| C08F 8/42 | (2006.01) | |
| C08K 5/20 | (2006.01) | |
| C08K 5/5419 | (2006.01) | |

(52) U.S. Cl.
CPC .............. *C08C 19/25* (2013.01); *B60C 1/00* (2013.01); *C07F 7/1804* (2013.01); *C08C 19/22* (2013.01); *C08F 8/30* (2013.01); *C08F 8/42* (2013.01); *C08F 36/04* (2013.01); *C08K 5/00* (2013.01); *C08K 5/16* (2013.01); *C08K 5/20* (2013.01); *C08K 5/54* (2013.01); *C08K 5/5419* (2013.01); *Y02T 10/862* (2013.01)

(58) Field of Classification Search
CPC .............. C08K 3/34; C08K 3/30; C08K 5/20
See application file for complete search history.

(56) References Cited

U.S. PATENT DOCUMENTS

| | | | | | |
|---|---|---|---|---|---|
| 6,001,948 | A | * | 12/1999 | Scheim | ................ C08K 5/5442 528/34 |
| 6,020,448 | A | * | 2/2000 | Jenkner | ................ C07F 7/1804 528/26 |
| 2005/0020757 | A1 | | 1/2005 | Ozawa et al. | |
| 2008/0255354 | A1 | | 10/2008 | Popp et al. | |
| 2009/0005498 | A1 | | 1/2009 | Lin et al. | |
| 2009/0236974 | A1 | | 9/2009 | Tamaru et al. | |
| 2011/0143966 | A1 | | 6/2011 | McGall et al. | |
| 2013/0085225 | A1 | * | 4/2013 | Nishioka | ............... B60C 1/0016 524/547 |
| 2013/0165350 | A1 | * | 6/2013 | Kuimelis | ................ C40B 50/18 506/32 |

FOREIGN PATENT DOCUMENTS

| | | | |
|---|---|---|---|
| CN | 105153219 A | 12/2015 | |
| DE | 19725501 C1 | 12/1998 | |
| FR | 2889702 A1 | * 2/2007 | ................ C08F 2/38 |
| JP | H11012469 A | 1/1999 | |
| JP | 2008531634 A | 8/2008 | |
| JP | 2010531383 A | 9/2010 | |
| JP | 2013093587 A | 5/2013 | |
| WO | 2003048216 A1 | 6/2003 | |
| WO | 2012011571 A1 | 1/2012 | |

OTHER PUBLICATIONS

Search report from International Application No. PCT/KR2016/015078, dated Mar. 31, 2017.
Liu, X, et al., "Preparation and evaluation of a hydrolytically stable amide-embedded stationary phase." Journal of Chromatography A, vol. 1119, Feb. 3, 2006, pp. 128-134.
Pukhalskaya, Vera G., et al., "Synthesis, structure and muscarinic agnoist activity of substituted N-(silatran-1-ylmethyl)acetamides." Applied Organometallic Chemistry, vol. 24, No. 3, 2010, pp. 162-168.
Database PubChem Compound [Online], "Compound Summary for CID 123866537-1,1,3-Tris [3-di (propan-2-yloxy)silylpropyl]urea", Jan. 25, 2017, Database accession No. CID 123866537, XP002782361.
Database PubChem Compound [Online], "Compound Summary for CID 87406544-KILSBXULRJSBJD-UHFFFAOYSA-N", Feb. 12, 2015, Database accession No. CID 87406544, XP002782360.
Extended European Search Report including Written Opinion for Application No. EP16879354.5 dated Jul. 27, 2018.

* cited by examiner

*Primary Examiner* — Mark S Kaucher
(74) *Attorney, Agent, or Firm* — Lerner, David, Littenberg, Krumholz & Mentlik, LLP

(57) ABSTRACT

The present invention provides a compound represented by Formula 1, a modified and conjugated diene-based polymer with a high modification ratio, which includes a functional group derived from the compound, a method for preparing the polymer, a rubber composition including the polymer, and a tire manufactured from the rubber composition.

19 Claims, No Drawings

MODIFIED AND CONJUGATED DIENE-BASED POLYMER AND METHOD FOR PREPARING THEREOF

TECHNICAL FIELD

Cross-Reference to Related Applications

The present application is a national phase entry under 35 U.S.C. § 371 of International Application No. PCT/KR2016/015078 filed on Dec. 22, 2016, which claims priority from Korean Patent Application No. 10-2015-0184240, filed on Dec. 22, 2015, the disclosures of which are incorporated herein by reference.

TECHNICAL FIELD

The present invention relates to a compound useful for modifying a polymer, a modified and conjugated diene-based polymer including a functional group derived from the compound, and a method for preparing the polymer.

BACKGROUND ART

According to the recent demand for cars having a low fuel consumption ratio, a conjugated diene-based polymer having modulational stability represented by wet skid resistance as well as low running resistance, and excellent abrasion resistance and tensile properties is required as a rubber material for tires.

In order to reduce the running resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, conjugated diene-based (co)polymers such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

If the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature.

The solution-polymerized SBR is prepared by using an anionic polymerization initiator and is being used by coupling or modifying the chain terminals of the polymer thus formed using various modifiers.

Meanwhile, carbon black and silica are being used as a reinforcing filler of a tire tread, wherein, if the silica is used as the reinforcing filler, low hysteresis loss and wet skid resistance may be improved. However, since the silica having a hydrophilic surface has a low affinity with a conjugated diene-based rubber in comparison to the carbon black having a hydrophobic surface, dispersibility may be poor, and thus, there is a need to use a separate silane coupling agent to improve the dispersibility or provide coupling between the silica and the rubber.

Therefore, attempt of introducing a functional group having affinity or reactivity with silica into the terminal of a rubber molecule is being performed, but its effect is insufficient.

In addition, if the affinity only with silica is improved, the affinity with carbon black is relatively degraded, and thus, the application range thereof may be limited.

Accordingly, the development of rubbers having high affinity with carbon black as well as silica is required.

DISCLOSURE OF THE INVENTION

Technical Problem

The present invention has been devised in consideration of the above-mentioned limitations, and an object of the present invention is to provide a compound useful for modifying a polymer.

Another object of the present invention is to provide a modified and conjugated diene-based polymer with a high modification ratio.

Further another object of the present invention is to provide a method for preparing the modified and conjugated diene-based polymer.

Technical Solution

To solve the above-described tasks, there is provided in the present invention a compound represented by the following Formula 1:

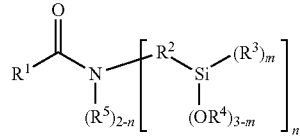

[Formula 1]

in Formula 1, $R^1$ is a monovalent hydrocarbon group of 1 to 20 carbon atoms, or a monovalent hydrocarbon group of 1 to 20 carbon atoms, which includes at least one heteroatom selected from the group consisting of N, S and O, $R^2$ is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, $R^3$ to $R^5$ are each independently a monovalent hydrocarbon group of 1 to 20 carbon atoms, m is an integer of 0 to 2, and n is an integer of 1 or 2.

In addition, according to another embodiment of the present invention, there is provided a modified and conjugated diene-based polymer including a functional group derived from a compound represented by the following Formula 1:

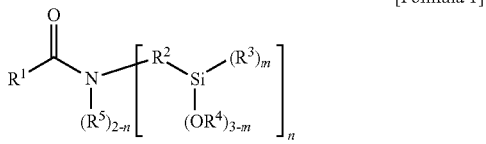

[Formula 1]

in Formula 1,

R¹ is a monovalent hydrocarbon group of 1 to 20 carbon atoms, or a monovalent hydrocarbon group of 1 to 20 carbon atoms, which includes at least one heteroatom selected from the group consisting of N, S and O, R² is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, R³ to R⁵ are each independently a monovalent hydrocarbon group of 1 to 20 carbon atoms, m is an integer of 0 to 2, and n is an integer of 1 or 2.

Also, there is provided a method for preparing the modified and conjugated diene-based polymer, including a step of polymerizing conjugated diene-based monomers, or an aromatic vinyl-based monomer and a conjugated diene-based monomer in the presence of an organometal compound in a hydrocarbon solvent to prepare an active polymer which is bonded to an organometal (step 1); and a step of reacting the active polymer with a compound represented by the following Formula 1 (step 2):

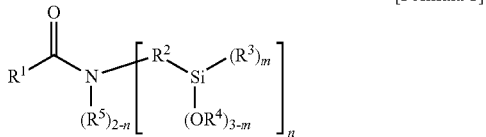

[Formula 1]

in Formula 1,

R¹ is a monovalent hydrocarbon group of 1 to 20 carbon atoms, or a monovalent hydrocarbon group of 1 to 20 carbon atoms, which includes at least one heteroatom selected from the group consisting of N, S and O, R² is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, R³ to R⁵ are each independently a monovalent hydrocarbon group of 1 to 20 carbon atoms, m is an integer of 0 to 2, and n is an integer of 1 or 2.

Advantageous Effects

The compound represented by Formula 1 according to the present invention introduces an acyl group and has high anionic reactivity, and thus, may easily interact with an active part of a polymer, thereby conducting modification easily.

In addition, the modified and conjugated diene-based polymer according to the present invention includes a functional group derived from a compound represented by Formula 1, for example, a tertiary amine group and a group having affinity with silica or affinity with hexane, and the affinity with a filler such as silica may become excellent and a high modification ratio may be achieved.

In addition, since the method for preparing a modified and conjugated diene-based polymer according to the present invention uses a compound represented by Formula 1, a modified and conjugated diene-based polymer with a high modification ratio may be easily prepared due to high solubility of the compound.

BEST MODE FOR CARRYING OUT THE INVENTION

Hereinafter, the present invention will be described in more detail in order to assist the understanding on the present invention.

It will be understood that words or terms used in the specification and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The present invention provides a compound which is useful for modifying a conjugated diene-based polymer.

The compound according to an embodiment of the present invention is characterized in being represented by the following Formula 1:

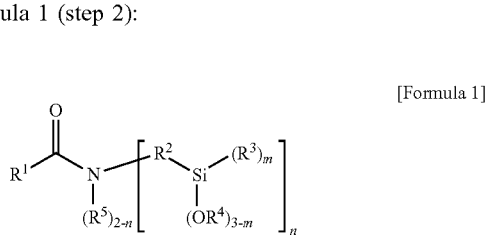

[Formula 1]

in Formula 1,

R¹ is a monovalent hydrocarbon group of 1 to 20 carbon atoms, or a monovalent hydrocarbon group of 1 to 20 carbon atoms, which includes at least one heteroatom selected from the group consisting of N, S and O, R² is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, R³ to R⁵ are each independently a monovalent hydrocarbon group of 1 to 20 carbon atoms, m is an integer of 0 to 2, and n is an integer of 1 or 2.

The compound represented by Formula 1 is a functional group which is capable of improving the physical properties of a polymer, and may include a functional group for improving dispersibility of an inorganic filler, and at least one of a functional group which has affinity with an inorganic filler and a functional group which has affinity with a solvent.

Particularly, the compound represented by Formula 1 may modify a polymer in a high modification ratio due to the inclusion of an acyl group which shows high reactivity with respect to an active part of an active polymer, and as a result, a functional group which is substituted in the compound may be introduced in a polymer with a high yield. In addition, the compound may include an amino group, particularly, a tertiary amino group as a functional group which may improve dispersibility of an inorganic filler by preventing the agglomeration of the inorganic filler in a rubber composition. For example, if silica is used as the inorganic filler, agglomeration may easily arise due to hydrogen bonds between hydroxyl groups present at the surface thereof. In contrast, the dispersibility of silica may be improved, because the tertiary amino group in the modifier may inhibit hydrogen bonds between hydroxyl groups. In addition, in addition to the amino group, the modifier may include at least one of a functional group which has affinity with an inorganic filler which may improve abrasion resistance and processability of a rubber composition due to the interaction with the inorganic filler, and a functional group which has affinity with a solvent and shows excellent affinity with a solvent used for the modification reaction of a polymer. The functional group which has affinity with the inorganic filler may particularly be an alkoxysilyl group which may undergo condensation reaction, after being introduced into the polymer, with a functional group at the surface of the inorganic filler, for example, in case where the inorganic filler is silica, with a silanol group at the surface of the silica, thereby improving the abrasion resistance and processability of the polymer. Such improving effects may be further improved with the increase of the number of the alkoxysilyl group. In addition, the functional group which has affinity with a solvent may particularly be a hydrocarbon group such as an alkyl group and an aryl group, and may improve the solubility of a compound in a solvent during the modification reaction of a conjugated diene-based copolymer, thereby improving the modification ratio of a polymer.

Particularly, in Formula 1, $R^1$ may be a monovalent hydrocarbon group of 1 to 20 carbon atoms, or a monovalent hydrocarbon group of 1 to 20 carbon atoms, which includes at least one heteroatom selected from the group consisting of N, S and O.

If $R^1$ is the monovalent hydrocarbon group of 1 to 20 carbon atoms, $R^1$ may be selected from the group consisting of an alkyl group of 1 to 20 carbon atoms, a cycloalkyl group of 3 to 20 carbon atoms, an aryl group of 6 to 20 carbon atoms, and an arylalkyl group of 7 to 20 carbon atoms, and in particular, $R^1$ may be selected from the group consisting of an alkyl group of 1 to 10 carbon atoms, a cycloalkyl group of 3 to 12 carbon atoms, an aryl group of 6 to 12 carbon atoms, and an arylalkyl group of 7 to 12 carbon atoms.

In addition, if $R^1$ is the monovalent hydrocarbon group of 1 to 20 carbon atoms, which includes a heteroatom, $R^1$ may include a heteroatom instead of at least one carbon atom in the hydrocarbon group; or may be a hydrocarbon group in which at least one hydrogen atom bonded to a carbon atom in the hydrocarbon group is substituted with a heteroatom or a functional group containing a heteroatom, where the heteroatom may be selected from the group consisting of N, O and S. Particularly, if $R^1$ is the monovalent hydrocarbon group of 1 to 20 carbon atoms, which includes a heteroatom, $R^1$ may be an alkoxy group; a phenoxy group; a carboxyl group; an acid anhydride group; an amino group; an amide group; an epoxy group; a mercapto group; —$[R^{11}O]xR^{12}$ (where $R^{11}$ is an alkylene group of 2 to 20 carbon atoms, $R^{12}$ is selected from the group consisting of a hydrogen atom, an alkyl group of 1 to 20 carbon atoms, a cycloalkyl group of 3 to 20 carbon atoms, an aryl group of 6 to 20 carbon atoms and an arylalkyl group of 7 to 20 carbon atoms, and x is an integer of 2 to 10); or a hydrocarbon group of 1 to 20 carbon atoms including at least one functional group selected from the group consisting of a hydroxyl group, an alkoxy group, a phenoxy group, a carboxyl group, an ester group, an acid anhydride group, an amino group, an amide group, an epoxy group and a mercapto group (for example, a hydroxyalkyl group, an alkoxyalkyl group, a phenoxyalkyl group, an aminoalkyl group, or a thiolalkyl group). More particularly, if $R^1$ is an alkyl group of 1 to 20 carbon atoms, which includes a heteroatom, $R^1$ may be selected from the group consisting of an alkoxy group of 1 to 20 carbon atoms, an alkoxyalkyl group of 2 to 20 carbon atoms, a phenoxyalkyl group of 7 to 20 carbon atoms, an aminoalkyl group of 1 to 20 carbon atoms, and —$[R^{11}O]xR^{12}$ (where $R^{11}$ is an alkylene group of 2 to 10 carbon atoms, $R^{12}$ is selected from the group consisting of a hydrogen atom, an alkyl group of 1 to 10 carbon atoms, a cycloalkyl group of 3 to 12 carbon atoms, an aryl group of 6 to 18 carbon atoms and an arylalkyl group of 7 to 18 carbon atoms, and x is an integer of 2 to 10).

In addition, in Formula 1, $R^2$ is a divalent hydrocarbon group of 1 to 20 carbon atoms, and particularly, may be an alkylene group of 1 to 10 carbon atoms such as a methylene group, an ethylene group and a propylene group; an arylene group of 6 to 20 carbon atoms such as a phenylene group; or an arylalkylene group of 7 to 20 carbon atoms as the combination thereof. More particularly, $R^2$ may be an alkylene group of 1 to 6 carbon atoms. More particularly, $R^2$ may be an alkylene group of 1 to 5 carbon atoms. In addition, $R^2$ may be substituted with at least one substituent selected from the group consisting of an alkyl group of 1 to 20 carbon atoms, a cycloalkyl group of 3 to 20 carbon atoms, and an aryl group of 6 to 30 carbon atoms.

In addition, in Formula 1, $R^3$ to $R^5$ may be each independently a monovalent hydrocarbon group of 1 to 20 carbon atoms, and may particularly be selected from the group consisting of an alkyl group of 1 to 10 carbon atoms, a cycloalkyl group of 3 to 18 carbon atoms, an aryl group of 6 to 18 carbon atoms and a combination thereof. More particularly, $R^3$ and $R^4$ may be each independently an alkyl group of 1 to 5 carbon atoms, and $R^5$ may be an alkyl group of 1 to 5 carbon atoms or a cycloalkyl group of 3 to 8 carbon atoms. More particularly, $R^3$ to $R^5$ may be each independently an alkyl group of 1 to 5 carbon atoms.

In addition, in Formula 1, m may be an integer of 0 to 2, and n may be an integer of 1 or 2.

More particularly, in the compound of Formula 1, $R^1$ is any one selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms, an aminoalkyl group of 1 to 10 carbon atoms, and $[R^{11}O]xR^{12}$ (where $R^{11}$ is an alkylene group of 2 to 10 carbon atoms, $R^{12}$ is selected from the group consisting of a hydrogen atom, an alkyl group of 1 to 10 carbon atoms, a cycloalkyl group of 3 to 12 carbon atoms, an aryl group of 6 to 18 carbon atoms and an arylalkyl group of 7 to 18 carbon atoms, and x is an integer of 2 to 10), $R^2$ is an alkylene group of 1 to 6 carbon atoms, $R^3$ and $R^4$ are each independently an alkyl group of 1 to 5 carbon atoms, $R^5$ is an alkyl group of 1 to 5 carbon atoms or a cycloalkyl group of 3 to 8 carbon atoms, m is an integer of 0 to 2, and n is an integer of 1 to 2, where if $R_1$ is the alkyl group of 1 to 10 carbon atoms, the cycloalkyl group of 3 to 10 carbon atoms, the aryl group of 6 to 12 carbon atoms, or the arylalkyl group of 7 to 12 carbon atoms, n may be an integer of 2.

More particularly, the compound represented by Formula 1 may be one selected from the group consisting of N,N-bis(3-triethoxysilyl)propyl)acetamide), N-methyl-N-(3-trimethoxysilyl)propyl)acetamide, N,N-bis(3-(diethoxymethylsilyl)propyl)acetamide and N-butyl-N-(3-(trimethoxysilyl)propyl)acetamide.

In addition, the compound may have a solubility of 10 g or more with respect to 100 g of a non-polar solvent, for example, hexane at 25° C. under 1 atm. Here, the solubility of the compound means the degree of clear dissolution without turbidity when observed with a naked eye. With such high solubility, an excellent modification ratio with respect to a polymer may be shown.

The compound according to the present invention has an optimized functional group which may maximize affinity with an inorganic filler and a solvent, and may be used as a modifier of a conjugated diene-based polymer to provide the conjugated diene-based polymer with excellent viscoelasticity, tensile properties and processability.

Meanwhile, the compound may be used as a modifier for modifying a conjugated diene-based polymer, and the conjugated diene-based polymer may be a homopolymer including a derived unit of a conjugated diene-based monomer or a copolymer including derived units of a conjugated diene-based monomer and an aromatic vinyl-based monomer.

In the present invention, the term "derived unit" may mean a component or a structure derived from a certain material, or the material itself.

In addition, the present invention provides a modified and conjugated diene-based polymer including a functional group derived from a compound represented by the following Formula 1:

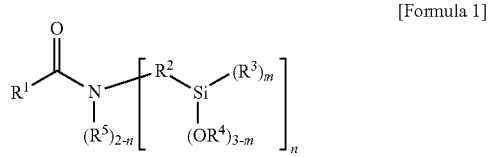

[Formula 1]

in Formula 1, $R^1$ is a monovalent hydrocarbon group of 1 to 20 carbon atoms, or a monovalent hydrocarbon group of 1 to 20 carbon atoms, which includes at least one heteroatom selected from the group consisting of N, S and O, $R^2$ is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, $R^3$ to $R^5$ are each independently a monovalent hydrocarbon group of 1 to 20 carbon atoms, m is an integer of 0 to 2, and n is an integer of 1 or 2.

The modified and conjugated diene-based polymer according to an embodiment of the present invention may be prepared by reacting an active polymer bonded to an organometal and the compound represented by Formula 1 via a preparation method described later, and the modified and conjugated diene-based polymer may have improved physical properties by including a functional group derived from the compound represented by Formula 1.

Particular examples of the compound represented by Formula 1 may be the same as described above.

Meanwhile, the modified and conjugated diene-based polymer may be a homopolymer or a copolymer. If the modified and conjugated diene-based polymer is the homopolymer, the modified and conjugated diene-based polymer may be a modified and conjugated diene polymer, and if the modified and conjugated diene-based polymer is the copolymer, the modified and conjugated diene-based polymer may include a derived unit of a conjugated diene-based monomer and a derived unit of an aromatic vinyl-based monomer. In addition, if the modified and conjugated diene-based polymer is the copolymer, the copolymer may be a random copolymer.

In the present invention, the term "random copolymer" may mean an arranged state of constituent units of the copolymer in disorder.

The conjugated diene-based monomer is not specifically limited, but may be at least one selected from the group consisting of 1,3-butadiene, 2,3-dimethyl-1,3-butadiene, piperylene, 3-butyl-1,3-octadiene, isoprene and 2-phenyl-1,3-butadiene.

If the modified and conjugated diene-based polymer is a copolymer, the copolymer may include the derived unit of a conjugated diene-based monomer in an amount of 40 wt % or more, particularly, 60 wt % to 90 wt %, more particularly, 60 wt % to 85 wt %.

The aromatic vinyl-based monomer is not specifically limited, but may be at least one selected from the group consisting of, for example, styrene, α-methyl styrene, 3-methyl styrene, 4-methyl styrene, 4-propylstyrene, 1-vinylnaphthalene, 4-cyclohexylstyrene, 4-(p-methylphenyl) styrene and 1-vinyl-5-hexylnaphthalene.

If the modified and conjugated diene-based polymer is a copolymer, a derived unit of an aromatic vinyl-based monomer may be included in an amount of 60 wt % or less, particularly, 10 wt % to 40 wt %, more particularly, 15 wt % to 40 wt %.

In addition, the modified and conjugated diene-based polymer may have a number average molecular weight of 1,000 g/mol to 2,000,000 g/mol, particularly, 10,000 g/mol to 2,000,000 g/mol, more particularly, 100,000 g/mol to 2,000,000 g/mol.

The modified and conjugated diene-based polymer may have molecular weight distribution (Mw/Mn) of 1.05 to 10, particularly, 1.1 to 5, more particularly, 1.1 to 4. If the modified and conjugated diene-based polymer has the molecular weight distribution, processability of a rubber composition including thereof may be improved, and as a result, the mechanical properties, low fuel consumption ratio properties and abrasion resistance of molded articles thus manufactured may be improved.

Here, the number average molecular weight is a polystyrene converted molecular weight which is analyzed by gel permeation chromatography (GPC), and the molecular weight distribution (Mw/Mn) is also referred to as polydispersity and may be obtained by measuring a weight average molecular weight (Mw) and a number average molecular weight (Mn), respectively, using a gel permeation chromatography and then, calculating a ratio (Mw/Mn) of the measured weight average molecular weight to the number average molecular weight.

In addition, the modified and conjugated diene-based polymer may have a vinyl content of 5 wt % or more, particularly, 10 wt % or more, more particularly, 14 wt % to 70 wt %. If the modified and conjugated diene-based copolymer shows the vinyl content in the above range, a glass transition temperature may be controlled in an appropriate range, and if applied to a tire, physical properties required for the tire such as running resistance and braking force may be satisfied, and effects of decreasing fuel consumption may be achieved.

Here, the vinyl content means an amount of not 1,4-added but 1,2-added conjugated diene-based monomer with respect to 100 wt % of a conjugated diene-based copolymer which is composed of a monomer having a vinyl group and an aromatic vinyl-based monomer.

In addition, the present invention provides a method for preparing a modified and conjugated diene-based polymer including a functional group derived from a compound represented by Formula 1.

The preparation method according to an embodiment of the present invention is characterized in including a step of polymerizing conjugated diene-based monomers, or an aromatic vinyl-based monomer and a conjugated diene-based monomer in the presence of an organometal compound in a hydrocarbon solvent to prepare an active polymer which is bonded to an organometal (step 1); and a step of reacting the active polymer with a compound represented by the following Formula 1 (step 2):

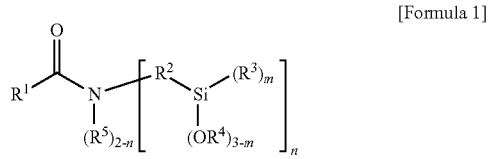

[Formula 1]

in Formula 1, $R^1$ is a monovalent hydrocarbon group of 1 to 20 carbon atoms, or a monovalent hydrocarbon group of 1 to 20 carbon atoms, which includes at least one heteroatom selected from the group consisting of N, S and O, $R^2$ is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, $R^3$ to $R^5$ are each independently a monovalent hydrocarbon group of 1 to 20 carbon atoms, m is an integer of 0 to 2, and n is an integer of 1 or 2.

Step 1 is a step for preparing an active polymer which is bonded to an organometal and may be conducted by polymerizing conjugated diene-based monomers, or a conjugated diene-based monomer and an aromatic vinyl-based monomer in the presence of an organometal compound in a hydrocarbon solvent.

The active polymer may represent a polymer in which a polymer anion and an organometal cation are bonded.

Particular kind of the conjugated diene-based monomer and the aromatic vinyl-based monomer may be the same as described above, and the amount used of each monomer may be determined by appropriately controlling the derived unit of the conjugated diene-based monomer and the derived unit of the aromatic vinyl-based monomer in the modified and conjugated diene-based copolymer within the above-described range.

The hydrocarbon solvent is not specifically limited but may be, for example, at least one selected from the group consisting of n-pentane, n-hexane, n-heptane, isooctane, cyclohexane, toluene, benzene and xylene.

The organometal compound may be an organo alkali metal compound or at least one selected from the group consisting of an organolithium compound, an organosodium compound, an organopotassium compound, an organorubidium compound and an organocesium compound.

Particularly, the organometal compound may be at least one selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide.

The organometal compound may be used in an amount of 0.01 mmol to 10 mmol based on total 100 g of the monomers. Particularly, the organometal compound may be used in an amount of 0.05 mmol to 5 mmol, more particularly, 0.1 mmol to 2 mmol, further more particularly, 0.1 mmol to 1 mmol based on total 100 g of the monomers.

The polymerization of step 1 may be conducted by further adding a polar additive, if needed, and the polar additive may be added in an amount of 0.001 g to 50 g, particularly, 0.001 g to 10 g, more particularly, 0.005 g to 0.1 g based on total 100 g of the monomers.

In addition, the polar additive may be added in an amount of 0.001 g to 10 g, particularly 0.005 g to 1 g, more particularly, 0.005 g to 0.1 g based on total 1 mmol of the organometal compound.

The polar additive may be a salt, an ether, an amine or a mixture thereof, particularly, may be at least one selected from the group consisting of tetrahydrofuran, ditetrahydrofurylpropane, diethyl ether, cycloamyl ether, dipropyl ether, ethylene dimethyl ether, diethylene glycol, dimethyl ether, tert-butoxy ethoxy ethane, bis(3-dimethylaminoethyl) ether, (dimethylaminoethyl) ethyl ether, trimethylamine, triethylamine, tripropylamine, and tetramethylethylenediamine. More particularly, ditetrahydrofurylpropane, triethylamine, or tetramethylethylenediamine may be used.

By using the polar additive in the preparation method according to an embodiment of the present invention, if a conjugated diene-based monomer and an aromatic vinyl-based monomer are copolymerized, a difference of reaction rates between them may be compensated, thereby inducing easy formation of a random copolymer.

The polymerization of step 1 may be anionic polymerization, particularly, living anionic polymerization by which an active part is obtained by propagation reaction based on anions.

In addition, the polymerization may be temperature programmed polymerization, isothermal polymerization, or constant temperature polymerization (adiabatic polymerization).

Here, the constant temperature polymerization means a polymerization method including a step of polymerizing using self-generated heat of reaction without optionally applying heat after injecting an organometal compound, the temperature programmed polymerization means a polymerization method in which the temperature is increased by optionally applying heat after injecting an organometal compound, and the isothermal polymerization means a polymerization method in which the temperature of a polymer is kept constant by increasing heat by applying heat or taking heat after injecting an organometal compound.

The polymerization may be conducted in a temperature range of −20° C. to 200° C., and particularly, 0° C. to 150° C., and more particularly, may be conducted in a temperature range of 10° C. to 120° C.

Step 2 is a step of reacting the active polymer with the compound represented by Formula 1 to prepare a modified and conjugated diene-based polymer.

The compound represented by Formula 1 may be the same as described above, and one kind or a mixture of two or more kinds thereof may be used in the reaction.

The compound represented by Formula 1 may be used in an amount of 0.1 mol to 10 mol based on 1 mol of the organometal compound. Particularly, the compound represented by Formula 1 may be used in an amount of 0.3 mol to 2 mol based on 1 mol of the organometal compound. If the compound is used in an amount within the ratio range, modification reaction with optimized performance may be conducted, and a conjugated diene-based polymer with a high modification ratio may be obtained.

The reaction of step 2 is modification reaction for introducing a functional group in a polymer and may be conducted at 0° C. to 90° C. for 1 minute to 5 hours.

In addition, the preparation method of the modified and conjugated diene-based polymer according to an embodiment of the present invention may be conducted by a batch type polymerization method or a continuous type polymerization method which includes at least one reactor.

The preparation method according to an embodiment of the present invention may further include at least one step among recovering a solvent and an unreacted monomer and drying after step 2, if needed.

Hereinafter, the present invention will be explained in more detail referring to embodiments and experimental embodiments. However, the following embodiments and experimental embodiments are only for the illustration of the present invention, and the scope of the present invention is not limited thereto.

PREPARATION EXAMPLE 1: PREPARATION OF N,N-BIS(2-(TRIETHOXYSILYL) PROPYL) ACETAMIDE

To a 100 ml round-bottom flask, 54.68 mmol of bis(triethoxysilylpropyl)amine (Gelest) was added and 30 ml of dichloromethane was added for dissolution, and 57.42 mmol of trimethylamine (Sigma-Aldrich) was added thereto, followed by stirring at 0° C. for 10 minutes under nitrogen conditions. Then, 54.68 mmol of acetyl chloride (DAEJUNG) was slowly injected for 30 minutes while conducting reaction, and reaction progress was checked by NMR in the middle of the reaction. After 4 hours, the reaction was finished, and 20 ml of a 5% sodium bicarbonate solution was added to extract an organic layer. Magnesium sulfate was added and drying and filtering were conducted to remove remaining water. After that, solvents were removed under a reduced pressure to obtain 50.82 mmol (yield 92.9%) of N,N-bis(2-(triethoxysilyl)propyl)acetamide of Formula (i) below. $^1$H nuclear magnetic resonance spectroscopic data of separated N,N-bis(2-(triethoxysilyl)propyl)acetamide are as follows.

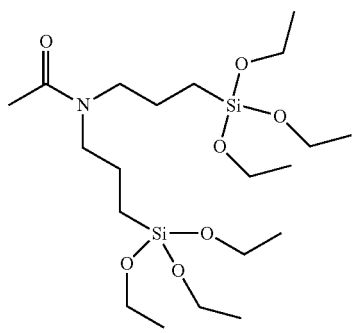

$^1$H-NMR (500 MHz, CDCl$_3$) δ 3.83-3.80 (m, 12H), δ 3.30-3.27 (t, 2H), δ 3.23-3.20 (t, 2H), δ 2.08 (s, 3H), δ 1.66-1.59 (m, 6H), δ 1.24-1.20 (m, 18H), δ 0.60-0.55 (m, 4H)

PREPARATION EXAMPLE 2: PREPARATION OF N-METHYL-N-(3-(TRIMETHOXYSILYL)PROPYL) ACETAMIDE

To a 100 ml round-bottom flask, 50.59 mmol of N-methylaminopropyltrimethoxysilane (Gelest) was added and 20 ml of dichloromethane was added for dissolution, and 60.71 mmol of trimethylamine (Sigma-Aldrich) was added thereto, followed by stirring at 0° C. for 10 minutes under nitrogen conditions. Then, 53.12 mmol of acetyl chloride (DAEJUNG) was slowly injected for 30 minutes while conducting reaction, and reaction progress was checked by NMR in the middle of the reaction. After 4 hours, the reaction was finished, and 20 ml of a 5% sodium bicarbonate solution was added to extract an organic layer. Magnesium sulfate was added, and drying and filtering were conducted to remove remaining water. After that, solvents were removed under a reduced pressure to obtain 42.99 mmol (yield 85.0%) of N-methyl-N-(3-(trimethoxysilyl)propyl)acetamide of Formula (ii) below. $^1$H nuclear magnetic resonance spectroscopic data of separated N-methyl-N-(3-(trimethoxysilyl)propyl)acetamide are as follows.

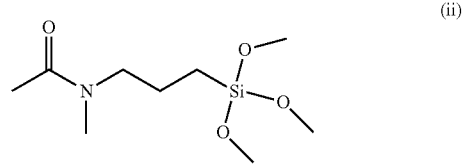

$^1$H-NMR (500 MHz, CDCl$_3$) δ 3.55 (s, 9H), δ 3.24-3.21 (t, 2H), δ 2.88 (s, 3H), δ 1.61-1.56 (m, 2H), δ 0.57-0.54 (t, 2H)

PREPARATION EXAMPLE 3: PREPARATION OF N,N-BIS(3-(DIETHOXY(METHYL)SILYL) PROPYL)ACETAMIDE

To a 250 ml round-bottom flask, 76.87 mmol of bis(methyldiethoxysilylpropyl)amine (Gelest) was added and 50 ml of dichloromethane was added for dissolution, and 115.31 mmol of trimethylamine (Sigma-Aldrich) was added thereto, followed by stirring at 0° C. for 10 minutes under nitrogen conditions. Then, 92.25 mmol of acetyl chloride (DAEJUNG) was slowly injected for 30 minutes while conducting reaction, and reaction progress was checked by NMR in the middle of the reaction. After 4 hours, the reaction was finished, and 60 ml of a 5% sodium bicarbonate solution was added to extract an organic layer. Magnesium sulfate was added and drying and filtering were conducted to remove remaining water. After that, solvents were removed under a reduced pressure to obtain 72.40 mmol (yield 94.2%) of N,N-bis(3-diethoxy(methyl)silyl)propyl)acetamide of Formula (iii) below. $^1$H nuclear magnetic resonance spectroscopic data of separated N,N-bis(3-diethoxy(methyl)silyl)propyl)acetamide are as follows.

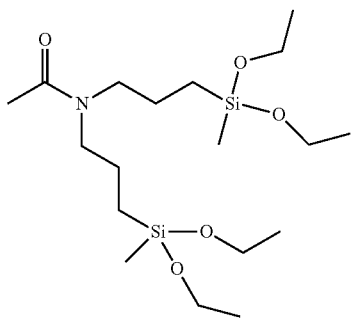

(iii)

$^1$H-NMR (500 MHz, CDCl$_3$) δ 3.74-3.72 (m, 8H), δ 3.27-3.24 (t, 2H), δ 3.20-3.17 (t, 2H), δ 2.05 (s, 3H), δ 1.61-1.54 (m, 2H), δ 0.55-0.52 (m, 2H), δ 0.09 (s, 6H)

PREPARATION EXAMPLE 4: PREPARATION OF N-BUTYL-N-(3-(TRIMETHOXYSILYL)PROPYL)ACETAMIDE

To a 250 ml round-bottom flask, 118.78 mmol of N-butylaminopropyltrimethoxysilane (Gelest) was added and 50 ml of dichloromethane was added for dissolution, and 187.17 mmol of trimethylamine (Sigma-Aldrich) was added thereto, followed by stirring at 0° C. for 10 minutes under nitrogen conditions. Then, 142.532 mmol of acetyl chloride (DAEJUNG) was slowly injected for 30 minutes while conducting reaction, and reaction progress was checked by NMR in the middle of the reaction. After 4 hours, the reaction was finished, and 60 ml of a 5% sodium bicarbonate solution was added to extract an organic layer. Magnesium sulfate was added and drying and filtering were conducted to remove remaining water. After that, solvents were removed under a reduced pressure to obtain 109.68 mmol (yield 92.3%) of N-butyl-N-(3-trimethoxysilyl)propyl)acetamide of Formula (iv) below. $^1$H nuclear magnetic resonance spectroscopic data of separated N-butyl-N-(3-(trimethoxysilyl)propyl)acetamide are as follows.

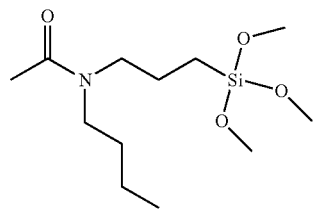

(iv)

$^1$H-NMR (500 MHz, CDCl$_3$) δ 3.58-3.56 (d, 9H), δ 3.30-3.28 (t, 2H), δ 3.22-3.19 (t, 2H), δ 2.07-2.06 (d, 3H), δ 1.69-1.61 (m, 2H), δ 1.55-1.46 (m, 2H), δ 0.96-0.90 (m, 3H), δ 0.62-0.57 (m, 2H)

EXAMPLE

To a 20 L autoclave reactor, 270 g of styrene, 710 g of 1,3-butadiene, 5 kg of n-hexane, and 1.26 g of 2,2-di(2-tetrahydrofuryl)propane (DTP) as a polar additive were added, and the internal temperature of the reactor was elevated to 40° C. When the internal temperature of the reactor reached 40° C., 42.1 g (2.62 wt % in hexane, 33% activation) of n-butyllithium was injected into the reactor, and an adiabatic reaction with heating was performed. After about 30 minutes, 710 g of 1,3-butadiene was injected for capping the terminal of SSBR with butadiene. After 5 minutes, 1.85 g of N,N-bis(2-(triethoxysilyl)propyl)acetamide prepared in Preparation Example 1 was injected, and reaction was conducted for 15 minutes ([DTP]/[act. Li]=1.3, [compound]/[act. Li]=0.74). Then, the polymerization reaction was quenched by adding ethanol, and 33 g of a solution in which 30 wt % of WINGSTAY® (Eliokem SAS, France) as an antioxidant was dissolved in hexane, was added thereto. The polymer thus obtained was added to hot water heated using steam and stirred to remove solvents, followed by roll drying to remove remaining solvents and water to prepare a modified styrene-butadiene copolymer.

COMPARATIVE EXAMPLE

To a 20 L autoclave reactor, 270 g of styrene, 710 g of 1,3-butadiene, 5 kg of n-hexane, and 1.26 g of 2,2-di(2-tetrahydrofuryl)propane (DTP) as a polar additive were added, and the internal temperature of the reactor was elevated to 40° C. When the internal temperature of the reactor reached 40° C., 42.1 g (2.62 wt % in hexane, 33% activation) of n-butyllithium was injected into the reactor, and an adiabatic reaction with heating was performed. After about 30 minutes, 710 g of 1,3-butadiene was injected for capping the terminal of SSBR with butadiene. Then, the polymerization reaction was quenched by adding ethanol, and 33 g of a solution in which 30 wt % of WINGSTAY (Eliokem SAS, France) as an antioxidant was dissolved in hexane, was added thereto. The polymer thus obtained was added to hot water heated using steam and stirred to remove solvents, followed by roll drying to remove remaining solvents and water to prepare a styrene-butadiene copolymer.

EXPERIMENTAL EXAMPLE

A weight average molecular weight (Mw), a number average molecular weight (Mn), molecular weight distribution (MWD), molecular weight of the highest peak (Mp) and coupling efficiency (%) on this case were measured for each of the modified styrene-butadiene copolymer and the styrene-butadiene copolymer prepared in the examples and the comparative example. The results are shown in Table 1 below.

The weight average molecular weight (Mw), the number average molecular weight (Mn) and the molecular weight of the highest peak (Mp) were measured by gel permeation chromatography (GPC) analysis, and the molecular weight distribution (MWD, Mw/Mn) was calculated from each of the measured molecular weights. In addition, the coupling efficiency (%) means a molecular weight ratio of 2-arm or more, and the molecular weight ratio of 2-arm or more was obtained by converting the total molecular weight of a modified styrene-butadiene copolymer, which is shown in a measured GPC graph into 100, and calculating the coupling ratio of at least two copolymers except for the coupling ratio of one copolymer in a multimodal with bimodal or more.

Particularly, the GPC used two columns of PLgel Olexis (Polymer Laboratories Co. Ltd.) and one column of PLgel mixed-C (Polymer Laboratories Co. Ltd.) in combination, and newly replaced columns were all mixed bed type columns. Polystyrene (PS) was used as a GPC standard material when calculating the molecular weights.

TABLE 1

| Division | Whether modified or not | GPC (×10⁴) | | | Coupling efficiency (%) | Molecular weight distribution (Mw/Mn) |
| | | Mn (g/mol) | Mw (g/mol) | Mp (g/mol) | | |
|---|---|---|---|---|---|---|
| Example | Modified | 25 | 40 | 19/72 | 40.4 | 1.58 |
| Comparative Example | Unmodified | 32 | 34 | 34 | — | 1.05 |

As shown in Table 1, it was found that the modified styrene-butadiene copolymer of the example, which was prepared using a modifier according to an embodiment of the present invention, had a higher molecular weight ratio of 2-arm or more, that is, higher long-chain coupling ratio than the styrene-butadiene copolymer of the comparative example.

Particularly, the modified styrene-butadiene copolymer of the example had a molecular weight ratio of 2-arm or more of 40.4%, and showed about 18% increase of a weight average molecular weight when compared to the styrene-butadiene copolymer of the comparative example. This is a result indicating that the compound according to an embodiment of the present invention included an amide group, and the reactivity with anions of a polymer chain was increased, and thus, a highly modified copolymer was formed.

The invention claimed is:

1. A compound represented by the following Formula 1:

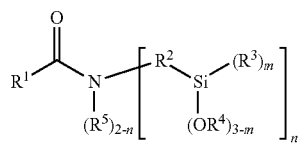

[Formula 1]

in Formula 1,
R¹ is selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms, and —[R¹¹O]$_x$R¹², where R¹¹ is an alkylene group of 2 to 10 carbon atoms, R¹² is selected from the group consisting of a hydrogen atom, an alkyl group of 1 to 10 carbon atoms, a cycloalkyl group of 3 to 12 carbon atoms, an aryl group of 6 to 18 carbon atoms, and an arylalkyl group of 7 to 18 carbon atoms, and x is an integer of 2 to 10,
R² is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms,
R³ to R⁵ are each independently a monovalent hydrocarbon group of 1 to 20 carbon atoms,
m is an integer of 0 to 2, and n is 2.

2. The compound of claim 1, wherein in Formula 1,
R² is an alkylene group of 1 to 6 carbon atoms,
R³ and R⁴ are each independently an alkyl group of 1 to 5 carbon atoms,
R⁵ is an alkyl group of 1 to 5 carbon atoms or a cycloalkyl group of 3 to 8 carbon atoms, and
m is an integer of 0 to 2.

3. The compound of claim 1, wherein in Formula 1,
R¹ is one selected from the group consisting of an alkyl group of 1 to 10 carbon atoms, an alkoxyalkyl group of 2 to 10 carbon atoms and a phenoxyalkyl group of 7 to 12 carbon atoms,
R² is an alkylene group of 1 to 5 carbon atoms,
R³ and R⁴ are each independently an alkyl group of 1 to 5 carbon atoms, and
m is an integer of 0 or 1.

4. The compound of claim 1, wherein the compound represented by Formula 1 is one selected from the group consisting of N,N-bis(3-triethoxysilyl)propyl)acetamide, and N,N-bis(3-(diethoxy(methyl)silyl)propyl)acetamide.

5. The compound of claim 1, wherein the compound is used as a modifier for modifying a conjugated diene-based polymer.

6. The compound of claim 5, wherein the conjugated diene-based polymer is a homopolymer comprising a derived unit of a conjugated diene-based monomer, or a copolymer comprising derived units of a conjugated diene-based monomer and an aromatic vinyl-based monomer.

7. A modified and conjugated diene-based polymer comprising a functional group derived from a compound represented by the following Formula 1:

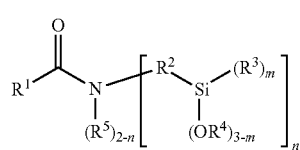

[Formula 1]

in Formula 1,
R¹ is selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms, an aminoalkyl group of 1 to 10 carbon atoms, and —[R¹¹O]$_x$R¹², where R¹¹ is an alkylene group of 2 to 10 carbon atoms, R¹² is selected from the group consisting of a hydrogen atom, an alkyl group of 1 to 10 carbon atoms, a cycloalkyl group of 3 to 12 carbon atoms, an aryl group of 6 to 18 carbon atoms, and an arylalkyl group of 7 to 18 carbon atoms, and x is an integer of 2 to 10,
R² is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms,
R³ to R⁵ are each independently a monovalent hydrocarbon group of 1 to 20 carbon atoms,
m is an integer of 0 to 2, and n is 2.

8. The modified and conjugated diene-based polymer of claim 7, wherein the compound represented by Formula 1 is one selected from the group consisting of N,N-bis(3-triethoxysilyl)propyl)acetamide, and N,N-bis(3-(diethoxy(methyl)silyl)propyl)acetamide.

9. The modified and conjugated diene-based polymer of claim 7, wherein the conjugated diene-based polymer is a homopolymer comprising a derived unit of a conjugated diene-based monomer, or a copolymer comprising derived units of a conjugated diene-based monomer and an aromatic vinyl-based monomer.

10. The modified and conjugated diene-based polymer of claim 9, wherein the copolymer comprises 60 wt % or less of the derived unit of the aromatic vinyl-based monomer.

11. The modified and conjugated diene-based polymer of claim 7, wherein the polymer has a number average molecular weight of 1,000 g/mol to 2,000,000 g/mol.

12. The modified and conjugated diene-based polymer of claim 7, wherein the polymer has molecular weight distribution (Mw/Mn) of 1.05 to 10.

13. The modified and conjugated diene-based polymer of claim 7, wherein the polymer has a vinyl content of 5 wt % or more.

14. A method for preparing a modified and conjugated diene-based polymer of claim 7, the method comprising:
1) a step of polymerizing conjugated diene-based monomers, or an aromatic vinyl-based monomer and a conjugated diene-based monomer in the presence of an organometal compound in a hydrocarbon solvent to prepare an active polymer which is bonded to an organometal; and
2) a step of reacting the active polymer with a compound represented by the following Formula 1:

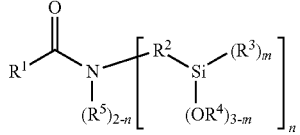

[Formula 1]

in Formula 1,
R$^1$ is selected from the group consisting of an alkyl group of 1 to 10 carbon atoms, a cycloalkyl group of 3 to 12 carbon atoms, an aryl group of 6 to 12 carbon atoms, an arylalkyl group of 7 to 12 carbon atoms, an alkoxyalkyl group of 2 to 10 carbon atoms, a phenoxyalkyl group of 7 to 12 carbon atoms, an aminoalkyl group of 1 to 10 carbon atoms, and —[R$^{11}$O]$_x$R$^{12}$, where R$^{11}$ is an alkylene group of 2 to 10 carbon atoms, R$^{12}$ is selected from the group consisting of a hydrogen atom, an alkyl group of 1 to 10 carbon atoms, a cycloalkyl group of 3 to 12 carbon atoms, an aryl group of 6 to 18 carbon atoms, and an arylalkyl group of 7 to 18 carbon atoms, and x is an integer of 2 to 10, R$^2$ is a divalent hydrocarbon group of 1 to 20 carbon atoms, which is unsubstituted or substituted with at least one substituent selected from the group consisting of an alkyl group of 1 to 20 carbon atoms, a cycloalkyl group of 3 to 20 carbon atoms, and an aryl group of 6 to 30 carbon atoms, R$^3$ to R$^5$ are each independently a monovalent hydrocarbon group of 1 to 20 carbon atoms, m is an integer of 0 to 2, and n is 2.

15. The method for preparing a modified and conjugated diene-based polymer of claim 14, wherein the organometal compound is used in an amount of 0.01 mmol to 10 mmol based on total 100 g of the monomers.

16. The method for preparing a modified and conjugated diene-based polymer of claim 14, wherein the polymerizing of step 1) is conducted by further adding a polar additive.

17. The method for preparing a modified and conjugated diene-based polymer of claim 16, wherein the polar additive is used in an amount of 0.001 g to 10 g based on total 1 mmol of the organometal compound.

18. The method for preparing a modified and conjugated diene-based polymer of claim 14, wherein the compound represented by Formula 1 is one selected from the group consisting of N,N-bis(2-triethoxysilyl)propyl)acetamide, and N,N-bis(3-(diethoxy(methyl)silyl)propyl)acetamide.

19. The method for preparing a modified and conjugated diene-based polymer of claim 14, wherein the compound represented by Formula 1 is used in an amount of 0.1 mol to 10 mol based on 1 mol of the organometal compound.

* * * * *